(12) United States Patent
Sanders

(10) Patent No.: US 6,390,016 B1
(45) Date of Patent: May 21, 2002

(54) SIGHT FLOW INDICATOR

(75) Inventor: Gary G. Sanders, Rock Falls, IL (US)

(73) Assignee: Penberthy, Inc., Prophetstown, IL (US)

( * ) Notice: Subject to any disclaimer, the term of this patent is extended or adjusted under 35 U.S.C. 154(b) by 0 days.

(21) Appl. No.: 09/370,506

(22) Filed: Aug. 9, 1999

(51) Int. Cl.[7] ............................................. G01F 15/06
(52) U.S. Cl. ......................................... 116/276; 96/416
(58) Field of Search .......................... 16/273, 274, 275, 16/276, 264; 356/440, 441, 442; 96/414–417, 422, 423; 285/93

(56) References Cited

U.S. PATENT DOCUMENTS

| | | | | |
|---|---|---|---|---|
| 1,902,659 A | * | 3/1933 | Muller-Clemm | 356/441 |
| 1,937,722 A | * | 12/1933 | Slmon et al. | 356/439 |
| 1,994,768 A | * | 3/1935 | Holven et al. | 356/339 |
| 2,046,113 A | * | 6/1936 | Gerdts | 436/2 |
| 2,650,562 A | * | 9/1953 | Bonar et al. | 116/276 |
| 2,692,528 A | * | 10/1954 | Uhl | 356/337 |
| 3,007,436 A | * | 11/1961 | Seaborne | 116/276 |
| 3,619,623 A | * | 11/1971 | Huston | 250/575 |
| 4,468,962 A | * | 9/1984 | Keech et al. | 73/200 |
| 4,725,289 A | * | 2/1988 | Quintilian | 95/76 |
| 5,048,325 A | * | 9/1991 | von Alfthan et al. | 73/61.41 |
| 5,599,365 A | * | 2/1997 | Alday et al. | 55/426 |
| 5,685,974 A | * | 11/1997 | Fleming | 210/95 |
| 5,872,622 A | * | 2/1999 | Schildmeyer et al. | 356/37 |
| 6,168,647 B1 | * | 1/2001 | Perry, Jr. et al. | 95/19 |
| 6,178,383 B1 | * | 1/2001 | Pegram et al. | 702/25 |

OTHER PUBLICATIONS

Premier Instruments, Inc., 10801 Hammerly, Suite 118, Houston, Tx, 77043, Red Eye Water Cut Meter with Flow Computer (Date Unknown).

* cited by examiner

*Primary Examiner*—Diego Gutierrez
*Assistant Examiner*—R. Alexander Smith
(74) *Attorney, Agent, or Firm*—Jenner & Block, LLC

(57) ABSTRACT

A sight flow indicator having a viewing window for monitoring liquid flowing therethrough is disclosed. The flow indicator is configured to disentrain gas and particulate from a portion of the fluid. The flow indicator is also configured to reduce the velocity of fluid flowing therethrough. The portion of the fluid from which gas and particulate has been disentrained is diverted from the main flow stream, past the viewing window. The relatively clean liquid sample flowing past the viewing window lends itself to relatively accurate optical analysis using, compared to the bulk fluid flowing through the flow indicator. The flow indicator is well-suited for use with a spectrometer or other optical analyzer.

17 Claims, 2 Drawing Sheets

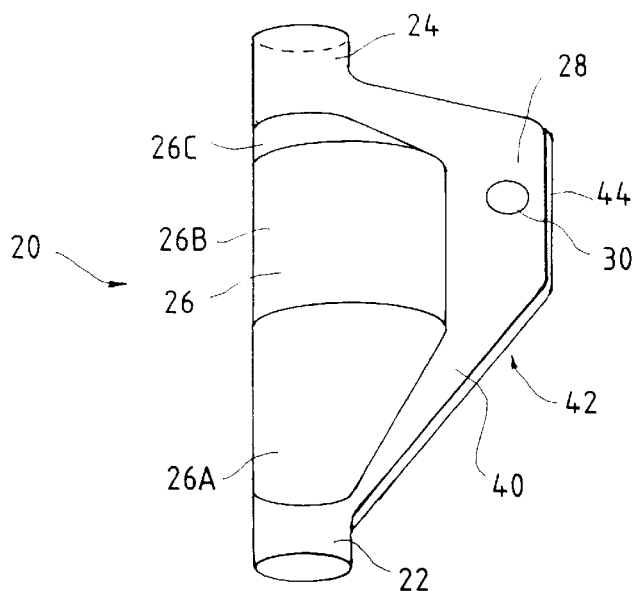
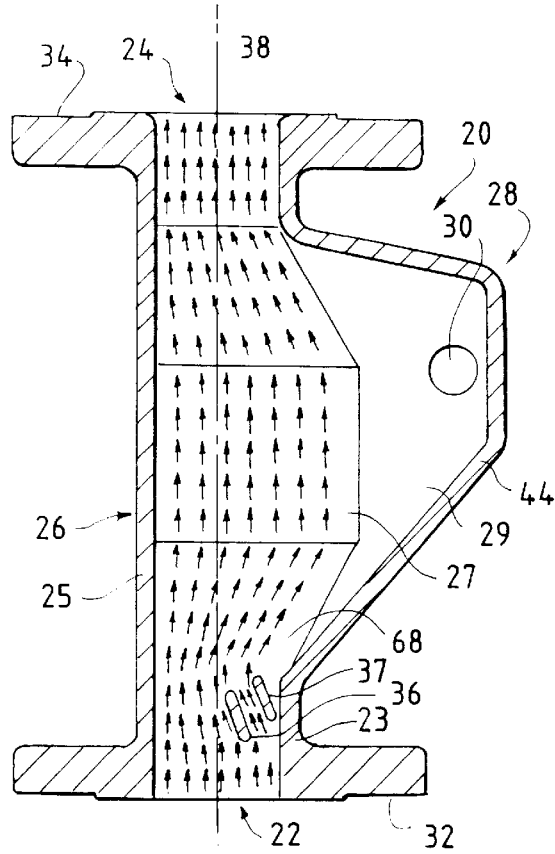
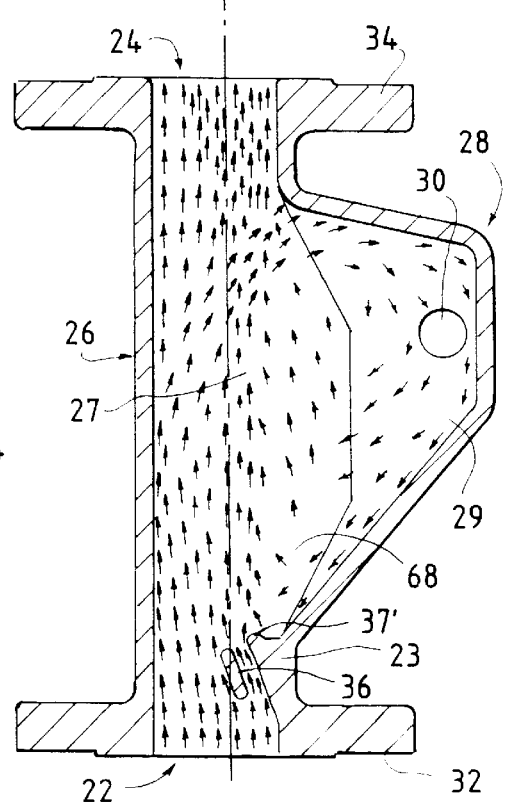

SIGHT FLOW INDICATOR

BACKGROUND OF THE INVENTION

The invention relates generally to piping specialty items. More particularly, the invention relates to a sight flow indicator which allows optical monitoring of fluid in a piping system.

Sight flow indicators have long been known in the art. Prior art sight flow indicators commonly comprise a transparent body or an armored metal body with one or more glass viewing ports, a fluid inlet port, and a fluid outlet port. Sight flow indicators are commonly used in piping systems, such as petrochemical piping systems, to allow an operator to visually monitor the flow of fluids therein. However, sight flow indicators generally permit monitoring of bulk fluid flow only and do not provide a ready indication of the constituents of the bulk flow. For example, oil pumped from a well is likely to include produced water, produced gases, sediment, and other particulate matter. Although a conventional sight flow indicator allows an operator to monitor such bulk well flow, an operator generally cannot determine visually what percentage of the bulk well flow comprises, for example, oil vs. produced water.

Prior art techniques for determining the composition of oil versus produced water in bulk oil well flow generally involve collecting the bulk flow or a sample thereof in a separation vessel, or tank, and allowing the gases, the produced oil, the produced water, and the sediment to separate and stratify (a process that can take several days). Once the produced water and oil have been separated, the relative percentages of each can be readily determined. However, this technique operates on a sampling, not continuous, basis, and it does not provide real-time data that may be of vital importance to a well operator.

Techniques have been developed for analyzing multi-fluid flow to determine the percentages of the various components present therein. One such technique involves optical analysis of the flowing fluid. The technique may be implemented by associating an optical analyzer, such as a spectrometer, with the viewing region of a conventional sight flow indicator so that the optical analyzer can monitor and analyze the fluid flowing through the pipeline. Although this technique offers analysis and data output on a real-time or near real-time basis, its accuracy suffers when the fluid contains entrained gas and particulate matter. Accordingly, it would be desirable to provide a sight flow indicator which can provide a substantially gas- and particulate-free sample to a viewing region of the sight flow indicator.

SUMMARY OF THE INVENTION

It is an object of the invention to provide a sight flow indicator for use in piping systems which provides optical indication of fluid flow therethrough.

It is another object of the invention to provide such a sight flow indicator which is configured to disentrain gas and particulate matter from at least a portion of the flow indicator which comprises a viewing window.

It is a further object of the invention to provide such a sight flow indicator which can be used in conjunction with an optical analyzer which can determine the relative percentages of different types of liquids, such as oil and produced water, comprising the bulk fluid flow through the sight flow indicator.

The apparatus of the present invention is a sight flow indicator which has an inlet port and an outlet port, with an expansion chamber disposed therebetween. The expansion chamber includes a diverging region, a main body portion, and a converging region. The diverging region is located between the inlet port and the main body of the expansion chamber, and the converging region is located between the main body of the expansion chamber and the outlet port. The main body of the expansion chamber has a relatively large cross section, compared to the inlet and outlet ports. In a preferred embodiment, one or more flow baffles are located within or near the inlet port, proximate the diverging region.

A sampling cavity extends radially outward from the main body of the expansion chamber. In a preferred embodiment, the sampling cavity is comma-shaped and has a thin cross section, compared to the main body of the expansion chamber, to allow for optical analysis of relatively opaque liquids, such as heavy crude oil. The sampling cavity includes one or more transparent viewing windows.

In use, the sight flow indicator is installed as an in-line element in a piping system. Typically, the inlet and outlet ports are sized to substantially match the inlet and outlet piping.

In a preferred embodiment and installation, the sampling cavity lies in a substantially horizontal plane and fluid flows through the flow indicator in a substantially horizontal direction. Also, in a preferred embodiment, a portion of the expansion chamber lies above the sampling cavity and a portion of the expansion chamber lies below the sampling cavity.

As a fluid flows through the inlet port and across the baffles, the fluid's velocity is increased and its pressure is reduced as a consequence of the reduced flow area proximate the baffles. This effect tends to disentrain gases from the fluid. As the fluid exits the inlet port and baffle region and flows into the expansion chamber, the fluid's flow velocity is reduced as a consequence of the increasing cross sectional area of the diverging section of the expansion chamber. As a consequence of the initial increase and subsequent decrease in flow velocity, and of the expansion chamber's overall configuration, gases entrained in the fluid tend to rise out of the fluid into an upper region of the expansion chamber, to a level above the sampling cavity. Similarly, solids and particulate matter entrained in the fluid tend to settle into a lower region of the expansion chamber, to a level below the sampling cavity.

As the fluid passes over the baffles, at least a portion of the fluid flow is diverted away from the bulk flow centerline. An eddy current is thus established within the expansion chamber and through the sampling cavity. A person or an optical device can view the flow through the viewing window in the sampling cavity.

Since the sampling cavity lies substantially between the upper and lower regions of the expansion chamber, and because entrained gases and solids have risen and settled into the upper and lower regions of the expansion chamber, respectively, the flow through the sampling cavity and past the viewing window is relatively free from entrained gas and particulate matter. Consequently, optical detection means can be readily employed to analyze and determine the makeup of the liquid flow past the viewing window.

As the fluid flows out of the expansion chamber and through the outlet port, the fluid flow reconverges. Gases and solids that were disentrained from the bulk flow stream in the expansion chamber are substantially flushed out of the expansion chamber and into the outlet piping. The fluid's flow velocity and flow pressure are returned toward their upstream levels, subject to pressure losses caused by the sight flow indicator apparatus. But for such pressure loss, the flow through the remainder of the piping system is substantially unaffected by the sight flow indicator.

BRIEF DESCRIPTION OF THE DRAWINGS

FIG. 1 is a perspective view of a sight flow indicator according to the present invention;

FIG. 2 is a cross-sectional side elevation view of a sight flow indicator according to the present invention;

FIG. 3 is a cross-sectional side elevation view of a sight flow indicator according to the present invention;

DETAILED DESCRIPTION OF THE PREFERRED EMBODIMENT

Figure 4:
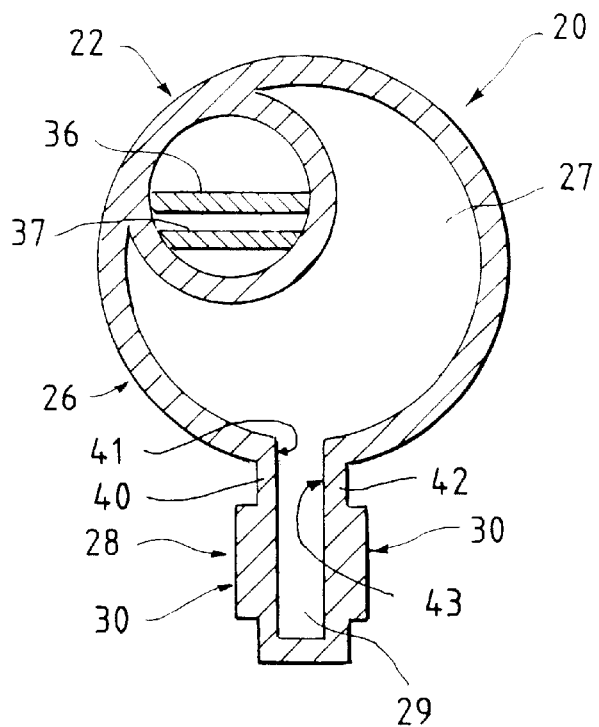
FIG. 4 is a cross-sectional elevation view of a sight flow indicator according to the present invention.

FIG. 1 illustrates a preferred embodiment of a sight flow indicator apparatus 20 according to the present invention. Apparatus 20 includes an inlet port 22, an outlet port 24, and an expansion chamber 26 which is located between inlet port 22 and outlet port 24. Inlet port 22 is shown as being coaxial with outlet port 24. In alternate embodiments, inlet port 22 may be offset from outlet port 24. Inlet port 22, outlet port 24, and expansion chamber 26 are illustrated as being substantially cylindrical, but they may take other shapes, as well.

In the embodiment illustrated in FIG. 2, apparatus 20 further includes an inlet port flange 32 adjacent to inlet port 22 and an outlet port flange 34 adjacent to outlet port 24. Inlet port flange 32 and outlet port flange 34 facilitate installation of apparatus 20 into a piping system (not shown).

Expansion chamber 26 has a diverging section 26A, a main body section 26B, and a converging section 26C. Diverging section 26A and converging section 26C are shaped like the frustum of a cone. In a preferred embodiment, diverging section 26A and converging section 26C are shaped like the frustum of an eccentric cone, while main body section 26B is substantially cylindrical. Consequently, the centerline of main body section 26B of expansion chamber 26 is offset from the centerlines of inlet port 22 and outlet port 24. In the illustrated embodiment, the offset is such that the perimeter of center section 26B is tangential with the perimeter of inlet port 22 and outlet port 24. In other embodiments of the invention, main body section 26B of expansion chamber 26 may be offset from inlet and outlet ports 22 and 24 to a greater or lesser degree. For example, main body section 26B of expansion chamber 26 can be coaxial with inlet and outlet ports 22 and 24.

A sampling cavity 28 projects radially from the perimeter of expansion chamber 26. Sampling cavity 28 has an interior region 29 of substantially rectangular cross section. In a preferred embodiment, sampling cavity 28 is substantially comma-shaped to promote steady, laminar sampling flow therethrough, as will be discussed below. Sampling cavity 28 is defined by a first side wall 40, a second side wall 42, and an end wall 44. End wall 44 extends about the perimeter of sampling cavity 28, except for that portion of the perimeter of sampling cavity 28 which abuts expansion chamber 26. Consequently, the interior region 29 of sampling cavity 28 is open to and communicates with the interior region 27 of expansion chamber 26.

As illustrated in FIGS. 1–5, each of side walls 40 and 42 of sampling cavity 28 contains a viewing port 30. Each viewing port 30 includes a counterbore 56, a land 58, and an aperture 46 defined by land 58. Each counterbore 56 includes internal threads 54. In a preferred embodiment, each land 58 is flush with the respective interior surface 41 an 43 of side wall 40 and 42.

A gasket 48 is located within counterbore 56, against land 58. Gasket 48 is substantially annular. The outside diameter of gasket 48 is slightly smaller than the diameter of counterbore 56 so that gasket 48 may be easily installed in and removed from counterbore 56, as desired. The inside diameter of gasket 48 is substantially the same as the diameter of aperture 46.

Figure 5:
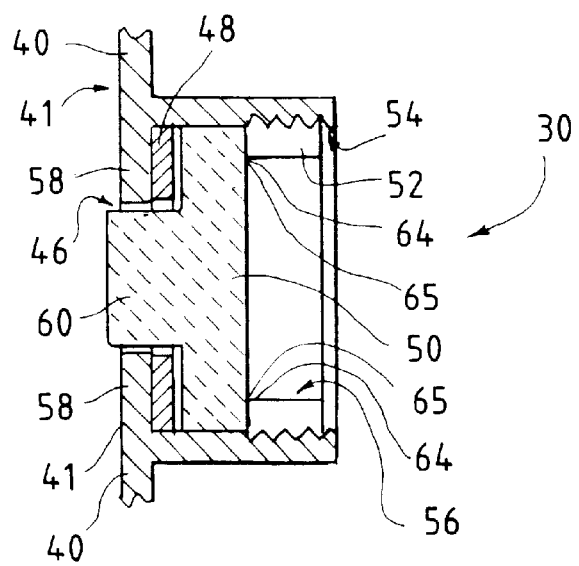
FIG. 5 is a cross-sectional side elevation view of a viewing port according to the present invention.

A transparent viewing window 50 is located within each counterbore 56, against gasket 48. In a preferred embodiment, as illustrated in FIG. 5, viewing window 50 resembles a flat disc having a protruding portion 60 which protrudes from one surface of the disc. Protruding portion 60 is shaped and sized to extend through gasket 48 and aperture 46. When viewing window is tightened against gasket 48, as will be explained below, protruding portion 60 of viewing window 50 extends slightly beyond the respective interior surface 41 or 43 of side wall 40 or 42. In an alternate embodiment, protruding portion 60 of viewing window 50 may be flush with the respective interior surface 41 or 43 of side wall 40 or 42. In another alternate embodiment, viewing window S0 may be a d with substantially flat sides which does not penetrate gasket 48 or aperture 46.

A viewing window retainer 52 holds each viewing window 50 in place within counterbore 56. In a preferred embodiment, viewing window retainer 52 is an externally threaded annular cylinder. A protective washer 64 and cushioning gasket 65 are installed between viewing window 50 and viewing window retainer 52. Viewing window retainer 52 is threaded into counterbore 56 and tightened against viewing window 50. Viewing window 50 in turn compresses gasket 48 against land 58, thus forming a leak-tight seal between viewing window 50 and walls 40 and 42 of sampling cavity 28.

Viewing port 30 is configured to allow an optical analyzer, such as a spectrometer (not shown), to be adapted thereto.

In the embodiments illustrated in FIGS. 2 and 3, a first elongated flow baffle 36 is located within inlet port 22, near the transition from inlet port 22 to diverging section 26C of expansion chamber 26. Flow baffle 36 spans two points on the inside perimeter of inlet port 22. See FIG. 4. In the embodiment illustrated in FIGS. 2 and 4, a second flow baffle 37 is similarly located and spans two other points on the inside perimeter of inlet port 22. In the embodiment illustrated in FIG. 3, flow baffle 37' is integral with a portion of side wall of inlet port 22. Other embodiments may have more or fewer than two flow baffles and may or may not include a flow baffle which is integral with side wall 23 of inlet port 22.

In a preferred embodiment, first and second flow baffles 36 and 37 (or 36 and 37') are substantially parallel to each other and are inclined at an angle of about 15° from the flow axis in a direction away from sampling cavity 28. In other embodiments, flow baffles 36 and 37 (or 36 and 37') may be set at other angles which cause diversion and turbulent mixing of a fluid flowing across them. First and second flow baffles 36 and 37 (or 36 and 37') need not be parallel to each other.

The components of sight flow indicator 20 can be made of any suitable material. Gasket 48 and cushioning gasket 65 can be made of any conventional gasket material. Viewing window 50 can be made of tempered glass or any other suitable transparent, optical quality material. Protective washer 64 can be made of steel, polymer, or other suitable load-bearing material. Viewing window retainer may also be made of steel, polymer, or other suitable material. The remaining components of sight flow indicator 20 can be made of any materials suitable for use in the piping system in which sight flow indicator 20 is to be installed. Such materials typically comprise various grades of steel or polymer, but other materials may be selected, as well.

An embodiment of sight flow indicator 20 having inlet and outlet flanges 32 and 34, such as that shown in FIGS. 2 and 3, can be bolted into a piping system (not shown) having mating flanges. Alternative embodiments of sight flow indicator 20 can be installed into a piping system in any suitable manner, such as by threaded connection or by welding.

In the Figures, inlet port 22 and outlet port 24 are illustrated as being of the same size. In practice, inlet port 22 and outlet port 24 are typically sized to match the inlet and outlet piping, respectively (not shown). The inlet and outlet piping may be the same size, or of different sizes. Consequently, inlet port 22 and outlet port 24 need not be the same size.

In a typical piping system installation, it is preferred that sight flow indicator 20 be installed such that fluid flows through sight flow indicator 20 in a substantially horizontal direction. It is also preferred that sight flow indicator 20 be installed such that sampling cavity 28 is substantially horizontal.

In operation, as illustrated by flow arrows 66 in FIG. 2, fluid flows predominantly from the upstream portion of the piping system (not shown), through inlet port 22, across flow baffles 36 and 37, through expansion chamber 26, and through outlet port 24 into the downstream portion of the piping system (not shown). As fluid flows through inlet port 22 and across baffles 36 and 37, the fluid's velocity is increased and its pressure is reduced as a consequence of the reduced flow area proximate the baffles. This effect tends to disentrain gases from the fluid. As the fluid exits inlet port 22 and flows into expansion chamber 26, the fluid's flow velocity is reduced as a consequence of the increasing cross sectional area of diverging section 26A of expansion chamber 26. As a consequence of the initial increase and subsequent decrease in flow velocity, the corresponding initial decrease and subsequent increase in pressure, and the overall configuration of expansion chamber 26, gases entrained in the fluid tend to rise out of the fluid into an upper region of expansion chamber 26, to a level above sampling cavity 28. Similarly, solids and particulate matter entrained in the fluid tend to settle into a lower region of expansion chamber 26, to a level below sampling cavity 28.

Although the fluid predominantly flows through sight flow indicator 20 as described above and as illustrated in FIG. 2, a portion of the fluid, hereinafter referred to as the cross-channel flow, is diverted through sampling cavity 28. As the flowing fluid crosses flow baffles 36 and 37 (or 36 and 37', as shown in FIG. 3), the flow baffles tend to divert the fluid away from the flow centerline and towards side wall 25 of expansion chamber 26. A portion of the flow thus diverted, i e the cross-channel flow, is directed towards and impinges side wall 25. After impinging side wall 25, the cross-channel flow is re-diverted across the main flow channel. The main flow tends to impel this cross-channel flow towards and into the main body section 26B of expansion chamber 26 and towards the end of sampling cavity 28 near the outlet end of expansion chamber 26.

The main flow and cross-channel flow paths are shown by the flow arrows 66 in FIG. 3. Although FIG. 3 illustrates an embodiment of a sight flow indicator 20 having a flow baffle 37' integral with side wall 23 of inlet port 22, the foregoing concepts also apply to embodiments having only non-integral flow baffles, such as those illustrated in FIG. 2.

As the fluid flows across flow baffles 36 and 37 (or 36 and 37') and is diverted towards the side wall of expansion chamber 26, a reduced-pressure region 68 is created near flow baffles 36 and 37 (or 36 and 37'). The pressure in reduced-pressure region 68 is somewhat lower than the pressure in the region immediately downstream of flow baffles 36 and 37 (or 36 and 37'). The reduced pressure in reduced-pressure region 68 tends to draw the cross-channel flow through the sampling cavity, and towards reduced-pressure region 68, adjacent to flow baffles 36 and 37 (or 36 and 37'). The main flow immediately downstream of flow baffles 36 and 37 (or 36 and 37') then tends to reentrain the cross-channel flow back into the main flow stream. This merged flow then substantially proceeds towards and through outlet port 24, although a portion of the merged flow may again be diverted through the sampling cavity as described above.

Since entrained gases and solids respectively tend to rise and settle out of the flow stream above and below the plane in which sampling cavity 28 lies as a result of the decreased flow velocity and the configuration of expansion chamber 26, the liquid which passes through sampling cavity 28 tends to be relatively free of entrained gases and solids. As such, the flow through sampling cavity 28 tends to be in a better condition for optical sampling than does the bulk flow with its entrained gases and solids.

Since transparent viewing windows 50, in the preferred embodiment, project slightly beyond of the interior surfaces 41 and 43 of first and second walls 40 and 42 of sampling cavity 28, it is relatively unlikely that particulate will accumulate on the viewing windows. However, in the event that particulate does accumulate on viewing windows 50, the liquid flowing through sampling cavity 28 and past viewing windows 50 tends to "wash" the viewing windows of such substances. Since the flow velocity through expansion chamber 26 and sampling cavity 28 is reduced from the flow velocity in the inlet piping due to the increased cross sectional area of expansion chamber 26, the likelihood of flow-induced damage to the viewing windows is also reduced.

Flow reconverges at the outlet end of the expansion chamber. As the fluid flows through converging section 26C of expansion chamber 26 and through outlet port 24, the flow velocity increases towards the entry velocity. As a consequence of the increased flow velocity and the configuration of expansion chamber 26, disentrained gases and particulate matter tend to be swept back into the main flow stream and into the outlet piping (not shown).

Although a specific embodiment of the invention is described herein, the scope of the invention is limited only by the claims appended hereto. It is understood that those skilled in the art may make modifications to the embodiments described herein without departing from the spirit of the invention.

I claim:

1. A piping element for use in connection with a fluid including a liquid and entrained gaseous and particulate matter, comprising:

a fluid inlet port for admitting said fluid into said piping element;

separation means for disentraining at least a substantial portion of said entrained gaseous and particulate matter from said fluid so as to produce a liquid sample substantially free of said entrained gaseous and particulate matter;

a viewing region to allow optical viewing of said liquid sample;

means for re-entraining substantially all of said disentrained gaseous and particulate matter into said fluid; and a fluid outlet port for outputting said fluid from said piping element.

2. The piping element of claim 1 wherein said separation means comprises an expansion chamber disposed between said inlet port and said outlet port.

3. The piping element of claim 2 further comprising a sampling cavity operably associated with said expansion chamber.

4. The piping element of claim 3 wherein said viewing region is operably associated with said sampling cavity.

5. The piping element of claim 3 further comprising at least one fluid baffle configured to cause a portion of said flowing fluid to be diverted toward said sampling cavity.

6. The piping element of claim 5 wherein said fluid baffle is proximate said inlet port.

7. A sight flow indicator apparatus for use in connection with a flowing fluid including a liquid and entrained gaseous and particulate matter, comprising:

a fluid inlet port;

a fluid outlet port;

an expansion chamber disposed between said inlet port and said outlet port, said expansion chamber comprising means for disentraining a substantial portion of said gaseous and particulate matter from said fluid so as to produce a liquid sample substantially free of said entrained gaseous and particulate matter and means for re-entraining substantially all of said gaseous and particulate matter into said fluid;

a sampling cavity coextensive with and in communication with said expansion chamber; and a liquid sample viewing region operably associated with said sampling cavity.

8. The apparatus of claim 7 further comprising a fluid baffle disposed proximate said inlet port, said fluid baffle being configured to divert flow toward said sampling cavity.

9. The apparatus of claim 8 wherein said fluid baffle is disposed within said inlet port.

10. The apparatus of claim 8 wherein said fluid baffle is set at an angle of about 15 degrees relative to the fluid flow axis through said inlet port.

11. The apparatus of claim 7 wherein said sampling cavity is substantially comma-shaped.

12. The apparatus of claim 7 further comprising a fluid baffle disposed proximate said inlet port, said fluid baffle being configured to divert at least a portion of said liquid sample out of and then across the flow stream defined by said flowing fluid so as to direct said portion of said liquid sample toward said sampling cavity.

13. The apparatus of claim 7 further comprising means for diverting at least a portion of said liquid sample toward said sampling cavity.

14. The apparatus of claim 7 further comprising means for diverting at least a portion of said liquid sample toward said sampling cavity, for drawing said at least a portion of said liquid sample through said sampling cavity, and for reintroducing said at least a portion of said liquid sample into said flowing fluid.

15. A method for providing a liquid sample relatively free of gaseous and particulate matter to a viewing window in a piping element, comprising the steps of:

admitting a fluid including a liquid and entrained gaseous and particulate matter to an expansion chamber, wherein said particulate matter tends to fall to a lower region of said expansion chamber, and wherein said gaseous matter tends to rise to an upper region of said expansion chamber, so as to produce said liquid sample relatively free of entrained gaseous and particulate matter;

directing at least a portion of said liquid sample proximate said viewing window; and reentraining substantially all of said gaseous and particulate matter into said fluid.

16. A piping element for use in connection with a fluid comprising a plurality of immiscible liquids and entrained gaseous and particulate matter, comprising:

a fluid inlet port for admitting said fluid into said piping element;

separation means for disentraining substantially all of said entrained gaseous and particulate matter from said fluid so as to produce a liquid sample comprising said plurality of immiscible liquids and substantially free of said entrained gaseous and particulate matter;

mixing means for mixing said plurality of immiscible liquids;

a viewing region to allow optical viewing of said liquid sample;

means for re-entraining substantially all of said disentrained gaseous and particulate matter into said fluid; and a fluid outlet port for outputting said fluid from said piping element.

17. The apparatus of claim 16 wherein a first of said plurality of immiscible liquids comprises oil and a second of said plurality of immiscible liquids comprises water.

* * * * *

UNITED STATES PATENT AND TRADEMARK OFFICE
CERTIFICATE OF CORRECTION

PATENT NO. : 6,390,016 B1
DATED : May 21, 2002
INVENTOR(S) : Gary G. Sanders

It is certified that error appears in the above-identified patent and that said Letters Patent is hereby corrected as shown below:

<u>Column 4,</u>
Line 26, delete "S0" and insert -- 50 --
Line 26, delete "d" and insert -- disk --

<u>Column 5,</u>
Line 59, delete "i e" and insert -- i.e. --

Signed and Sealed this

Nineteenth Day of November, 2002

*Attest:*

*Attesting Officer*

JAMES E. ROGAN
*Director of the United States Patent and Trademark Office*